United States Patent [19]

Tafesh et al.

[11] Patent Number: 5,223,640
[45] Date of Patent: Jun. 29, 1993

[54] PREPARATION OF OPTICALLY ACTIVE α-ARYL PROPIONIC ACIDS

[75] Inventors: Ahmed M. Tafesh; Sambasivarao Kotha; Kenneth G. Davenport, all of Corpus Christi, Tex.

[73] Assignee: Hoechst Celanese Corporation, Somerville, N.J.

[21] Appl. No.: 996,335

[22] Filed: Dec. 23, 1992

[51] Int. Cl.$^5$ .................... C07C 62/06; C07C 53/134; C07C 63/33
[52] U.S. Cl. .................... 562/466; 562/490; 562/496; 562/469; 562/492
[58] Field of Search ............... 562/466, 490, 496, 469, 562/492

[56] References Cited

U.S. PATENT DOCUMENTS 4,135,051  1/1979  Walker et al. .................. 562/496
4,801,719  1/1989  Oertle ............................ 562/496
5,097,061  3/1992  Shinizu et al. ................. 562/496
5,189,208  2/1993  Stahly ............................ 562/466

FOREIGN PATENT DOCUMENTS 460905   12/1991  European Pat. Off. .
3098944   8/1978  Japan .
7149242   9/1982  Japan .
7163337  10/1982  Japan .
3203631   8/1988  Japan .

*Primary Examiner*—Paul J. Killos
*Attorney, Agent, or Firm*—P. S. Kalyanaraman; James J. Mullen; Michael W. Ferrell

[57] ABSTRACT

This invention provides a process to prepare optically active α-aryl propionic acids without the need for resolving a racemic mixture. In one embodiment of the process, an acetophenone is sequentially converted to a 1-alkyne, then to an α-aryl β-silylated acrolein, and then to an acrylic acid, which is then asymmetrically hydrogenated to an optically active α-aryl propionic acid.

23 Claims, No Drawings

PREPARATION OF OPTICALLY ACTIVE α-ARYL PROPIONIC ACIDS

CROSS-REFERENCE TO RELATED APPLICATION

The subject matter of this invention is related to that disclosed in copending Patent Application, Ser. No. 07/996,360, filed of even date herewith.

FIELD OF THE INVENTION

This invention relates to a novel method for the preparation of optically active α-aryl propionic acids starting from suitable aryl acetylenes. The method preferentially involves a combination of silyl carbonylation, and asymmetric hydrogenation, among other reactions, and affords optically active α-aryl propionic acids in high yields.

BACKGROUND OF THE INVENTION

α-Aryl propionic acids are well known pharmaceutical compounds and include such well known analgesics such as ibuprofen, naproxen, ketoprofen, flurbifrofen and the like. Ibuprofen (Formula I) and naproxen (Formula II) are well-known non-steroidal anti-inflammatory (NSAI) drugs.

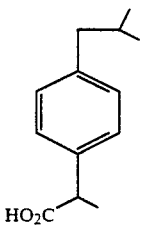

I

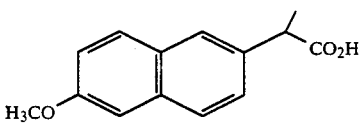

II

Several processes have been developed in the past to synthesize α-aryl propionic acids. For example, U.S. Pat. No. 4,981,995 describes the synthesis of ibuprofen by carbonylating 1-(4'-isobutylphenyl)ethanol. Jean-Pierre Rieu et al., *Tetrahedron* Vol. 42, No. 15, 4095-4131 (1986), and H. R. Sonawane et al. *Tetrahedron: Asymmetry*. Vol. 3, No. 2 163-192 (1992) review several general methods of synthesis of optically active α-aryl carboxylic acids.

Optically active forms of α-aryl propionic acids have been shown to exhibit therapeutic value greater than their racemic counterparts. Thus, for example, in the case of ibuprofen, the S(+)-enantiomer has been found to be more pharmacologically active than the racemic form, A. Avgerinos et al. *Chirality*. Vol. 2, 249 (1990). However, most of the known processes to prepare α-aryl propionic acids in general, and ibuprofen in particular, generally result in the formation of essentially the racemic form of such acids. This necessitates an extra step of resolving the racemic form into the enantiomers by elaborate resolution processes. U.S. Pat. Nos. 4,994,604 and 5,015,764 describe resolution processes to resolve racemic ibuprofen.

Due to the commercial significance of α-aryl propionic acids, there is an identified need for better and more economically viable synthetic processes to make them. Furthermore, it will be highly desirable if such processes yield the optically active forms of such acids directly, without the need to resolve a racemic mixture.

Thus, it is an object of this invention to provide an efficient and economic process to make α-aryl propionic acids.

It is a further object of this invention to provide a process which can be utilized to make the optically active forms of such acids directly without the need to resolve the racemic mixture.

SUMMARY OF THE INVENTION

One or more objects of the invention are achieved by providing a process to regioselectively prepare optically active α-aryl propionic acids which process comprises:

(a) silylcarbonylating an aryl acetylene of the formula Ar—C≡CH to form a α-aryl β-silylated acrolein of the formula

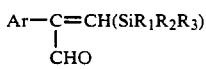

wherein $R_1$, $R_2$, and $R_3$ could be the same or different and are selected from the group consisting of hydrogen, a C1-C6 alkyl, a phenyl group, a naphthyl group and an alkoxy of the formula —OR' wherein R' is a $C_1$-$C_6$ alkyl, provided at least one of said $R_1$, $R_2$ and $R_3$ is not hydrogen; and (b) converting said silylated α-aryl acrolein to an α-aryl acrylic acid of the formula

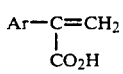

and, (c) regioselectively hydrogenating said acrylic acid to an optically active α-aryl propionic acid of the formula

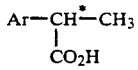

wherein * indicates an optically active center and Ar is an unsubstituted phenyl, or a phenyl substituted at the ortho position, the para position, or both the ortho and para positions, or an unsubstituted naphthyl moiety, or a naphthyl moiety substituted at one or more of the 1, 3, 6 and 7 positions, wherein the substituents are selected from the group consisting of alkoxy, acetoxy, acetamido, alkyl, phenyl and benzyl moieties, wherein the alkyl component is a branched or unbranched C1-C8 alkyl moiety, and said phenyl and benzyl substituents are optionally substituted with a C1-C8 alkyl or C1-C8 alkoxy moiety or both.

When Ar is 4'-isobutylphenyl in the above process, the starting material in step (a) would be 4'-isobutylphenyl acetylene and the product at the end of the reaction steps would be optically active ibuprofen. When Ar is 6-methoxynaphth-2-yl moiety, however, the product would be naproxen.

DESCRIPTION OF THE PREFERRED EMBODIMENTS

The invention discloses a novel process to directly make optically active α-aryl propionic acids, without the need for resolving a racemic mixture, unlike traditional processes which generally result in the racemic mixture of the R- and S- isomers.

In the inventive process, an aryl acetylene of the formula Ar—C≡CH (a 1-alkyne) is converted to a α-aryl β-silylated acrolein, which may then be converted to an α-aryl acrylic acid by suitable reaction steps. This is followed by asymmetric hydrogenation of the acrylic acid to yield optically active α-aryl propionic acid. Scheme 1 illustrates a preferred approach to prepare optically active ibuprofen, starting from a suitable aryl acetylene, with general utility for synthesizing similar optically active α-aryl propionic acids.

Scheme 1

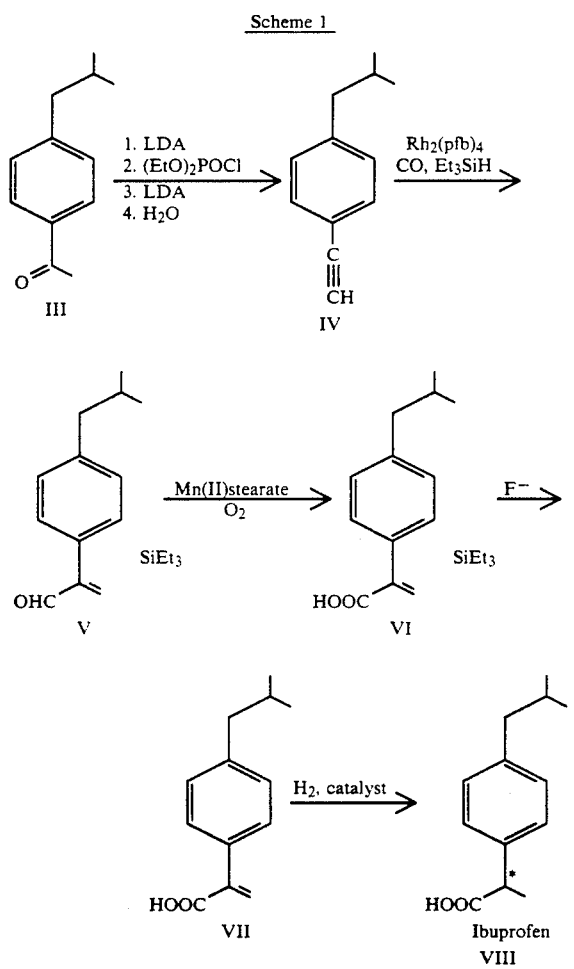

The inventive process starts with 4'-isobutylphenyl acetylene (Formula IV). Several such acetylenes are commercially available; if desired, they may be prepared by well known processes. A preferred preparative process is to make them by dehydrating unsubstituted or suitably substituted aromatic ketones such as, for example, acetophenones. Suitable dehydration reactions are reported by, for example, E. Negishi et al. *Organic Synthesis*, Vol. 64, 44 (1986), H. Staab et al. *Synthesis*. 424 (1974), and K. Evans et al. *Tetrahedron Lett.*, 6753 (1990). For example, compound of Formula IV may be prepared by dehydrating 4'-isobutylacetophenone (Formula III), by reacting with a halodialkylphosphate such as, for example, chlorodiethylphosphate in a base-catalyzed reaction, generally in a solvent. Preferred bases are lithium amides such as, for example, lithium diisopropylamide (LDA), sodamide, sodium acetate and the like. Preferred solvents are generally of the ether type solvents such as, for example, tetrahydrofuran (THF), and the reaction is conducted at around −80° to 20° C. At the end of the reaction, the reaction mixture may be poured into ice-water, and extracted with an organic solvent, which solvent is then removed to yield the desired acetylene.

Alternatively, the acetylene of Formula IV may be prepared by treating the ketone of Formula III with a Vilsmeier complex such as the one formed from N,N-dimethylformamide and POCl$_3$, following the procedure described by J. M. Watson, *Macromolecules*. Vol. 5, 331 (1972).

Conversion of 4'-isobutyl phenylacetylene (Formula IV) to an α-(4'-isobutylphenyl) β-silylated acrylic acid of Formula VI may be achieved by several processes. For example, *Chemistry Letters*. 523 (1990) describes a multistep process involving reactions with HBr, CO, Pd-tetraphenylphosphine catalyst, KOH and other reagents. A preferred approach involves first regioselectively silylcarbonylating the acetylene to a β-silylated acrolein (Formula V) by following the procedure disclosed in copending Patent Application, Ser. No. 07/996,360, filed on even date herewith, followed by oxidizing the acrolein to the corresponding acrylic acid of Formula VI. The procedure described in said copending Patent Application comprises reacting the acetylene with a suitable organosilane, carbon monoxide, and a suitable catalyst which is a carboxylate salt of rhodium, iridium or rhenium, in a suitable solvent. Suitable organosilanes are of the formula SiHR$_1$R$_2$R$_3$, wherein R$_1$, R$_2$ and R$_3$ could be the same or different and are selected from the group consisting of hydrogen, a C$_1$-C$_6$ alkyl, a phenyl group, a naphthyl group and an alkoxy of the formula —OR' wherein R' is a C$_1$-C$_6$ alkyl, provided at least one of said R$_1$, R$_2$ and R$_3$ is not hydrogen. Examples of suitable organosilanes include triethylsilane, trimethylsilane, tributylsilane, triphenylsilane and phenyldimethylsilane. Suitable solvents for the regioselective silylcarbonylation reaction are hydrocarbons, halogenated hydrocarbons, ethers, ketones, esters, and amides such as, for example, toluene, methylene chloride, N,N-dimethylformamide (DMF), tetrahydrofuran and the like. Preferred catalysts are the carboxylate salts of rhodium such as, for exaple, rhodium acetate, dirhodium (II) trifluoroacetate, dirhodium (II) perfluorobutyrate (Rh$_2$(pfb)$_4$), and the like.

The silylcarbonylation reaction may be conducted at low pressures of carbon monoxide, e.g., one atmosphere pressure, in which case the acetylene is preferentially added to the reaction mixture comprising the solvent, catalyst and the organosilane, and stirred. The reaction is generally performed at temperatures of about −30° C. to about 200° C., preferably at about −30° C. to about 100° C., and typically about −10° C. to about 30° C. After the addition of the alkyne, the reaction mixture is stirred at the same temperatures as above generally for about 1–100 hours, preferably for about 5–80 hours, and typically for about 24–72 hours. Alternatively, the reaction may be performed at higher pressures of carbon monoxide, in which case all the reactants may be taken together in a suitable pressure vessel such as, for example, an autoclave, and stirred under about 2-20 atmosphere pressures of carbon monoxide. Temperatures of about $-30°$ C. to about 300° C. may be employed for the reaction; generally higher temperatures tend to advantageously decrease the reaction time. Reaction times of about 0.5-100 hours may generally be employed. In either case, the silylcarbonylation reaction yields a regioselectively substituted α-(4'-isobutylphenyl) β-silylated acrolein of Formula V, in which the Z-isomer predominates, with substantial absence of hydrosilylation by-products. The term "predominates" means that the ratio of the Z-isomer to the E-isomer in the silylcarbonylated product ranges from about 5:1 to about 99:1. "Substantial absence of hydrosilylation by-products" means that not more than 10% hydrosilylation products are formed.

The silylcarbonylation step is followed by oxidizing the β-silylated acrolein to the corresponding acrylic acid (Formula VI). Oxidation of the acrolein to the acrylic acid may be achieved by several reagents such as, for example, potassium permanganate, silver oxide, manganese stearate, and the like, with manganese stearate being the preferred reagent. Oxidations with manganese stearate are discussed by D. P. Riley et al. *J. Organic Chem.*. Vol. 52, 287-290 (1987). Generally, the acrolein and the catalyst are mixed in a suitable solvent such as, for example, decane and reacted in an oxygen atmosphere at about $-10°$ C. to about 30° C., for a suitable time period such as, for example, 2-10 hours. The product may then be isolated from the reaction mixture by, for example, extraction into a solvent such as, for example, methylene chloride, dried, and the solvent may then be distilled off to yield the β-silylated acrylic acid of Formula VI.

The β-silylated acrylic acid may then be desilylated to the corresponding α-(4'-isobutylphenyl)acrylic acid (Formula VII). It is preferable to perform this reaction under conditions which do not disturb the stereochemistry around the double bond. A process such as, for example, the elimination reaction disclosed by T. H. Chan et al. *J. Organic Chem.*, Vol. 43, 1526-1532 (1978) is suitable. Such elimination reactions are catalyzed by halide salts, preferably fluoride salts. Thus, for example, the β-silylated acrylic acid may be dissolved in a suitable solvent such as, for example, acetonitrile or dimethyl sulfoxide, and stirred with an anhydrous fluoride salt such as, for example, tetramethylammonium fluoride, potassium fluoride and the like, at about $-10°$ C. to about 40° C. for about 2-10 hours, and then the product may be isolated by diluting with water, followed by filtration or extraction into a solvent to recover the desilylated acrylic acid.

The acrylic acid of Formula VII may then be asymmetrically hydrogenated to yield the optically active ibuprofen (Formula VIII). Asymmetric hydrogenations have been reviewed by W. S. Knowles in *Accts. Chem. Research.* Vol. 16, pages 106-112 (1983). Asymmetric hydrogenation of α-aryl acrylic acids to α-aryl propionic acids along with suitable catalysts for such hydrogenation is disclosed in U.S. Pat. No. 4,994,607 and International Publication No. WO 92/09552 (both assigned to Monsanto Co.). Generally the catalysts are metals such as rhodium or ruthenium complexed with ligands such as, for example, triphenylphosphine, 2,2'-bis(diphenylphosphino)-1,1'-binapthyl, cyclohexyl-o-anisyl-methylphosphine and 1,2-ethanediylbis [(o-methoxyphenyl)phenylphosphine. Use of such complexed ruthenium or rhodium catalysts such as, for example, Ru(OCOR)$_2$(binap) and [RuX(binap)(arene)]Y and rhodium 2,2'-bis (diphenylphosphino)-1,1'-binaphthyl (Rh-BINAP) in asymmetric hydrogenations is disclosed by H. Takaya et al. *Pure & Appl. Chem.*, Vol. 62, pages 1135-1138 (1990), B. D. Vineyard et al. *J. Amer. Chem. Soc.*, Vol. 99, pages 5946-5952 (1977), and A. Miyashita et al. *Tetrahedron*, Vol. 40, pages 1245-1253 (1984), and by R. Noyori et al., *J. Amer. Chem. Soc.*, Vol. 108, page 7117 (1986)). Such catalysts may be used in the asymmetric hydrogenation of the present invention. The reactions generally result in high optical purity of the hydrogenated product. Thus, for example, the acrylic acid of Formula VII may be hydrogenated by following the procedure of T. Ohta et al. *J. Organic Chem.*, Vol. 52, pp. 3174-3176 (1987). in a suitable solvent such as, for example, methanol, using the Rh-BINAP catalyst under hydrogen, at about 15°-40° C. for about 10-70 hours, resulting in optically active ibuprofen with high optical purity.

The following Examples are provided in order to further illustrate the present invention; however, the invention is in no way limited thereby.

EXAMPLES

In the following Examples, g refers to grams, ml to milliliters, °C. to degrees Celsius, mol to moles, mmol to millimoles, and ambient temperature to about 20°-28° C.

EXAMPLE 1

Preparation of 4'-isobutylchenyl acetylene (Formula IV) from 4'-isobutylacetophenone (Formula III)

LDA was prepared as follows. A 250 ml 3-neck round bottom flask, equipped with a magnetic stirring bar, an addition funnel, a thermometer, a rubber septum inlet and an outlet connected to a gas bubbler, was purged with nitrogen, and then charged with dry THF (50 ml). Diisopropylamine (7.7 ml, 55 mmol) was added and the contents were cooled with stirring to about 0° C. n-Butyllithium (n-BuLi) in hexane (1.6M, 33 ml) was added via a syringe, stirred at 0° C. for about 30 minutes, and then cooled to about $-78°$ C. (dry ice/ethyl acetate bath). To this mixture, a solution of 4'-isobutylacetophenone (prepared as in U.S. Pat. No. 4,981,995, 7 g, 40 mmol) in THF (50 ml) was added via the addition funnel over about 30 minutes. The reaction mixture was stirred for about 1 hour at about $-78°$ C., and then chlorodiethylphosphate (8 ml, 55 mmol) was added in one portion. The cooling bath was removed, and the contents were allowed to warm up to ambient temperature, whereat they were stirred for about 2.5 hours.

In a separate suitable flask, LDA was prepared as above from n-BuLi (1.6M in hexane, 66 ml) and diisopropylamine (15.4 ml), and was cooled to about $-78°$ C. under nitrogen. To this mixture was added, over about 40 minutes, the contents of the first flask via addition funnel, taking care that all operations and transfers were done under nitrogen. Then the reaction mixture was allowed to warm up to ambient temperature, whereat it was stirred for about 18 hours. The mixture was then poured on ice (about 200 g), diluted with water (about 300 ml), and extracted with hexane (3 × 150 ml). The combined organic layers were washed with 2N HCl (about 200 ml), brine (about 200 ml), and water (about 200 ml), and dried (MgSO$_4$). Removal of solvent in a rotary evaporator gave an oily product (7 g), which was found to be a mixture of the starting material and the product by thin layer chromatography (TLC) on silica gel (ethyl acetate: hexane-5:95 v/v as eluent). Column chromatography on silica gel with hexane elution afforded the desired acetylene product (3.1 g), pure enough for further reactions.

EXAMPLE 2

Preparation of 4'-isobutylchenyl acetylene by use of a Vilsmeier complex

A 1000 ml 3-neck flask was fitted with a mechanical stirrer, addition funnel and a thermometer. N,N-Dimethylformamide (103.92 g, 1.424 m) was added to the flask, stirred and cooled to about 0°-10° C. POCl$_3$ (129.80 g, 0.848 m) was added in one bulk, when the reaction mixture became yellow-colored. 4'-Isobutylphenyl acetylene (59.33 g, 0.337 m) was added and stirred, the mixture was warmed up to ambient temperature and stirred thereat for about 19 hours. Ice-water (300 g) was added to the reaction mixture, which was then extracted with diethyl ether (4×300 ml). The ether solution was dried (MgSO$_4$), and concentrated. GC analysis of the concentrate showed a high conversion of the starting ketone to the intermediate compound, β-chloro-β-(4'-isobutylphenyl) acrolein (approx. yield: 67.44 g), which could be converted to 4'-isobutylphenyl acetylene as follows.

Into a 1000 ml 3-neck flask fitted with a magnetic stirrer and addition funnel, the above intermediate acrolein compound was transferred with the aid of 1,4-dioxane (390 ml). The mixture was stirred for about 2 minutes at ambient temperature and then aqueous NaOH solution (10%, about 400 ml) was added, when the reaction mixture darkened in color. The reaction mixture was stirred at ambient temperature for about 20 hours and then acidified with concentrated HCl to pH about 5. The mixture was then extracted with diethyl ether (3×300 ml). The ether extracts were washed successively with water and saturated aqueous NaCl solution and dried (MgSO$_4$). Filtration and removal of ether from the filtrates yielded 4'-isobutylphenyl acetylene.

In a similar manner, 2-acetyl-6-methoxynaphthalene, 4-acetylbiphenyl, 4'-bromoacetophenone and 3,4-dimethoxyacetophenone were converted to the corresponding aryl acetylenes.

EXAMPLE 3

Preparation of α-(4'-isobutylphenyl)-β-triethysilyl acrolein in (Formula V)

This reaction may preferentially be performed by following the procedure described in copending Patent Application, Ser. No. 07/996,360, filed of even date herewith. A silylcarbonylation reaction under an atmospheric pressure of CO was performed as follows. In a 100 ml flask, fitted with a thermometer, a syringe pump for addition, gas inlet and outlet, triethylsilane (0.29 g, 2.5 mmol) was dissolved in dichloromethane (25 ml). Rh$_2$(pfb)$_4$ (0.3 mol% based on the phenyl acetylene) was added, and the reaction mixture was kept stirring under an atmospheric pressure of carbon monoxide (ambient pressure), while being cooled to about 0°-5° C. At the temperature, a solution of 4'-isobutylphenyl acetylene (2.5 mmol) in dichloromethane (5 ml) was added via the syringe pump over about 4-5 hours. After this time, the solvent was distilled off, and the product separated from the catalyst by column chromatography.

Purification was performed by vacuum distillation. Yield: 82%, with a 10:1 Z:E ratio.

EXAMPLE 4

Preparation of α-(4 -isobutylchenyl)-β-triethylsilyl acrylic acid (Formula VI)

This oxidation may be performed, for example, by following the procedure of D. P. Riley et al. referred to above. Thus, a suitable reaction vessel is charged with a solution of α-(4'-isobutylphenyl)-β-triethylsilyl acrolein (about 0.4M solution) in a suitable solvent such as, for example, chlorobenzene, and manganese stearate catalyst (to form a $6.0\times10^{-3}$ M solution), and then cooled to about 0° C. The vessel is then purged three times with O$_2$ (60 psi), and then the O$_2$ pressure is increased to about 120 psi. As oxygen is consumed, the pressure is increased back up to 120 psi. After about 3 hours of reaction, the gas is vented and about 5 ml of methylene chloride is added to dissolve the solids. Isolation and purification of the desired acrylic acid, and its analysis may be done by conventional methods.

EXAMPLE 5

Preparation of α-(4'-isobutylphenyl)acrylic acid (Formula VII)

This desilylation (elimination) reaction may be performed, for example, by following the procedure of T. H. Chan et al. referred to above. A catalyst such as, for example, potassium fluoride is used for desilylation. α-(4'-isobutylphenyl)-β-triethylsilyl acrylic acid from Example 4 (0.02 mol) is dissolved in a suitable solvent such as, for example, acetonitrile (15-20 ml). Potassium fluoride (0.025 mol) is added to the solution, and the mixture stirred at a suitable temperature such as, for example, ambient temperature, for a suitable time, for example, about 2-10 hours. The contents are poured into water (about 20 ml), and transferred to a separatory funnel. The separated organic layers are washed with water, then dried (with MgSO$_4$), and evaporated in vacuo to isolate the desilylated acrylic acid, which may be purified by conventional methods, if so desired.

EXAMPLE 6

Preparation of optically active ibuprofen (Formula VIII) by asymmetric hydrogenation of α-(4'-isobutylphenyl)acrylic acid This asymmetric hydrogenation may be carried out by following the procedure of T. Ohta et al. *J. Organic Chem.*, Vol. 52, 3174-3176 (1987). A 0.05M solution of α-(4'-isobutylphenyl)acrylic acid from Example 5 is prepared in a suitable solvent such as degassed absolute methanol in a suitable reaction vessel. Rh-BINAP catalyst prepared as in R. Noyori et al. *J. Amer. Chem. Soc.*, Vol. 108, 7117 (1986) is added in suitable amounts such that the ratio of the acrylic acid to catalyst is about 100-250. Hydrogenation is carried out under hydrogen pressure of about 10-150 atmos., at about 15°-35° C., over a period of about 10-70 hours. Removal of the catalyst, followed by removal of solvent yields optically active ibuprofen in high yields, which may be purified by conventional methods, if so desired.

In a similar manner, other α-aryl carboxylic acids such as naproxen, fenoprofen, indoprofen, ketoprofen, flurbiprofen, pirprofen, suprofen, cicloprofen, minoxiprofen and the like, may be prepared.

What is claimed is:

1. A process to prepare optically active α-aryl propionic acids, which comprises:
   (a) regioselectively silylcarbonylating an aryl acetylene of the formula Ar—C≡CH to form a silylated α-aryl acrolein of the formula Ar—C=CH(SiR$_1$R$_2$R$_3$)
   |
   CHO wherein R$_1$, R$_2$, and R$_3$ could be the same or different and are selected from the group consisting of hydrogen, a C1–C6 alkyl, a phenyl group, a naphthyl group, and an alkoxy of the formula —OR' wherein R' is a C$_1$–C$_6$ alkyl, provided at least one of said R$_1$, R$_2$, and R$_3$ is not hydrogen;
   (b) converting said silylated acrolein to an α-aryl acrylic acid of the formula Ar—C=CH$_2$
   |
   CO$_2$H and,
   (c) regioselectively hydrogenating said acrylic acid to an optically active α-aryl propionic acid, wherein Ar is an unsubstituted phenyl, or a phenyl substituted at the ortho position, the para position, or both the ortho and para positions, or an unsubstituted naphthyl moiety, or a naphthyl moiety substituted at one or more of the 1, 3, 6 and 7 positions, wherein the substituents are selected from the group consisting of alkoxy, acetoxy, acetamido, alkyl, phenyl and benzyl moieties, wherein the alkyl component is a branched or unbranched C1–C8 alkyl moiety, and said phenyl and benzyl substituents are optionally substituted with a C1–C8 alkyl or C1–C8 alkoxy moiety or both.

2. The process as described in claim 1, wherein Ar is 4'-isobutyl phenyl.

3. The process as described in claim 1, wherein said Ar is 6-methoxy-naphth-2-yl.

4. The process as described in claim 1, wherein said Ar is (3'-methoxyphenyl)phenyl.

5. The process as described in claim 1, wherein said Ar is 3-(3'-fluoro-4'-phenyl)phenyl.

6. The process as described in claim 1, wherein step (a) comprises reacting, in a suitable solvent at about −30° C. to about 300° C. for about 0.5–100 hours, with carbon monoxide, a silane of the formula SiHR$_1$R$_2$R$_3$, R$_1$, R$_2$ and R$_3$ being the same as in claim 1, and a catalyst which catalyst is a carboxylate salt of a metal selected from the group consisting of rhodium, iridium and rhenium.

7. The process as described in claim 6, wherein R$_1$, R$_2$ and R$_3$ are ethyl, and the catalyst is a carboxylate of rhodium.

8. The process as described in claim 7, wherein said rhodium carboxylate is dirhodium (II) perflurobutyrate, Rh$_2$[CF$_3$(CF$_2$)$_2$CO$_2$]$_4$.

9. The process as described in claim 6, wherein R$_1$ and R$_2$ are methyl and R$_3$ is phenyl, and said catalyst is dirhodium (II) perflurobutyrate, Rh$_2$[CF$_2$(CF$_3$)$_2$CO$_2$]$_4$.

10. The process as described in claim 1, wherein step (b) comprises: (i) oxidizing said acrolein to a silylated acrylic acid of the formula Ar—C=CH (SiR$_1$R$_2$R$_3$), and (ii) desilylating said silylated acrylic acid to said α-aryl acrylic acid, wherein R$_1$, R$_2$ and R$_3$ are the same as in claim 1.

11. The process as described in claim 10, wherein said oxidation in step (i) comprises reacting said acrolein with a reagent selected from the group consisting of silver nitrate, potassium permanganate, sodium cyanide, and manganese stearate in a suitable solvent, in oxygen atmosphere, at about −10° C. to about 30° C. for about 2-10 hours.

12. The process as described in claim 11, wherein said oxidizing reagent is manganese stearate and the solvent is decane.

13. The process as described in claim 10, wherein said desilylation in step (ii) comprises reacting with a reagent selected from the group consisting of potassium fluoride, tetrabutylammonium fluoride, hydrogen fluoride, tetrabutylammonium chloride, potassium chloride and tetrabutylammonium bromide, in a suitable solvent, at about −10° C. to about 40° C. for about 2-10 hours.

14. The process as described in claim 13, wherein said desilylation reagent is potassium fluoride, and said solvent is acetonitrile.

15. The process as described in claim 1, wherein step (c) comprises hydrogenation in presence of hydrogen catalyzed by ruthenium or rhodium, complexed with ligands selected from the group consisting of triphenylphosphine, 2,2'-bis(diphenylphosphino)-1,1'-binapthyl, cyclohexyl-o-anisyl-methylphosphine and 1,2-ethanediylbis[(o-methoxyphenyl)phenylphosphine, in a suitable solvent, at about 15°–35° C. for about 10–70 hours.

16. The process as described in claim 15, wherein said catalyst is rhodium complexed with 2,2'-bis(diphenylphosphino)-1,1'-binapthyl ligand, and said solvent is methanol.

17. A process to regioselectively prepare optically active α-aryl propionic acids, which comprises:
   (a) providing a ketone of the formula Ar—CO—CH$_3$ (b) converting said ketone to an alkyne of the formula Ar—C≡CH (c) converting said alkyne to an α-aryl acrolein of the formula Ar—C=CH(SiR$_1$R$_2$R$_3$)
   |
   CHO wherein R$_1$, R$_2$, and R$_3$ could be the same or different and are selected from the group consisting of hydrogen, a C1–C6 alkyl, a phenyl group, a naphthyl group and an alkoxy of the formula —OR' wherein R' is a C$_1$–C$_6$ alkyl, provided at least one of said R$_1$, R$_2$ and R$_3$ is not hydrogen;
   (d) oxidizing said acrolein to a silylated acrylic acid of the formula Ar—C=CH(SiR$_1$R$_2$R$_3$)
   |
   CO$_2$H wherein R$_1$, R$_2$ and R$_3$ are the same as above;
   (e) desilylating said silylated acrylic acid to an α-aryl acrylic acid of the formula

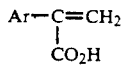

and, (f) regioselectively hydrogenating said acrylic acid of step (e) to an optically active α-aryl propionic acid, wherein Ar is an unsubstituted phenyl, or a phenyl substituted at the ortho position, the para position, or both the ortho and para positions, or an unsubstituted naphthyl moiety, or a naphthyl moiety substituted at one or more of the 1, 3, 6 and 7 positions, wherein the substituents are selected from the group consisting of alkoxy, acetoxy, acetamido, alkyl, phenyl and benzyl moieties, wherein the alkyl component is a branched or unbranched C1-C8 alkyl moiety, and said phenyl and benzyl substituents are optionally substituted with a C1-C8 alkyl or C1-C8 alkoxy moiety or both.

18. The process as described in claim 1, wherein Ar is 4'-isobutyl phenyl.

19. The process as described in claim 1, wherein said Ar is 6-methoxy-naphth-2-yl.

20. The process as described in claim 17, wherein said step (b) comprises first reacting said ketone with a base and a dialkylchlorophosphate in a suitable solvent at about −80° C. to about 20° C. to form an enol phosphate intermediate, followed by β-eliminating said enol phosphate intermediate to alkyne.

21. The process as described in claim 20, wherein said base is lithium diisopropylamide, said dialkylchlorophosphate is diethylchlorophosphate, and said solvent is tetrahydrofuran.

22. A process to regioselectively prepare optically active ibuprofen comprising:

(a) regioselectively silylcarbonylating an acetylene of the formula Ar—C≡CH in a suitable solvent, at about −30° C. to about 300° C. for about 0.5-100 hours, using carbon monoxide, a catalyst selected from the group consisting of a suitable carboxylate salt of rhodium, iridium, and rhenium, and a silane of the formula $SiHR_1R_2R_3$, wherein $R_1$, $R_2$ and $R_3$ could be the same or different and are selected from the group consisting of hydrogen, a C1-C6 alkyl, a phenyl group, a naphthyl group and an alkoxy of the formula —OR' wherein R' is a $C_1$-$C_6$ alkyl, provided at least one of said $R_1$, $R_2$ and $R_3$ is not hydrogen, to an α-aryl acrolein of the formula

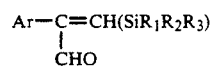

wherein $R_1$, $R_2$ and $R_3$ are as described above, and Ar is 4'-isobutylphenyl;

(b) converting said acrolein to α-(4'-isobutylphenyl)acrylic acid; and, (c) regioselectively hydrogenating said acrylic acid of step (b) in hydrogen atmosphere using a catalyst comprising rhodium complexed with 2,2'-bis(diphenylphosphino)- 1,1'-binapthyl in methanol solvent at about 15°-35° C. for about 10-70 hours to optically active ibuprofen.

23. The process as described in claim 22, wherein said catalyst in step (a) is dirhodium (II) perfluorobutyrate, and $R_1$, $R_2$ and $R_3$ are ethyl.

* * * * *